United States Patent [19]

Ishizuka et al.

[11] Patent Number: 5,096,924

[45] Date of Patent: Mar. 17, 1992

[54] ANTICANCER ANTIBIOTIC MI43-37F11 SUBSTANCE

[75] Inventors: Masaaki Ishizuka, Mishima; Hiroyuki Kumagai, Numazu; Tsutomu Sawa, Ayase; Hiroshi Naganawa, Tokyo; Hironobu Iinuma, Wako; Kunio Isshiki, Fujisawa; Masa Hamada, Tokyo; Kenji Maeda, Tokyo; Tomio Takeuchi, Tokyo, all of Japan

[73] Assignee: 501 Azidan Hojin Biseibutsu Kagaku Kenkyu Kai, Tokyo, Japan

[21] Appl. No.: 531,109

[22] Filed: May 31, 1990

[30] Foreign Application Priority Data

May 31, 1989 [JP] Japan .................. 1-136181

[51] Int. Cl.⁵ .............. A61K 31/35; C07D 311/76
[52] U.S. Cl. .................. 514/456; 549/289; 435/123
[58] Field of Search .............. 549/289; 514/456

[56] References Cited

PUBLICATIONS

Furutani et al., CA 87:113776x.
Umezawa et al., CA 89:197337g.

Primary Examiner—Jane T. Fan
Attorney, Agent, or Firm—Larson and Taylor

[57] ABSTRACT

As a new antibiotic is provided a compound, now nominated as MI43-37F11 substance, which has formula

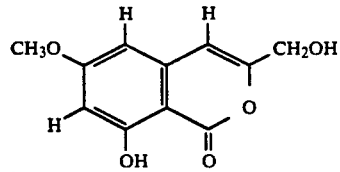

This MI43-37F11 substance has an antitumor activity, an activity to enhance the production of interleukin-1 in vivo in a mammalian, and an activity to activate a macrophage in vivo in a mammalian. MI43-37F11 substance may be produced by cultivation of *Streptoverticillium eurocidicum* MI43-37F11 strain identified as FERM BP-2783.

2 Claims, 3 Drawing Sheets

ANTICANCER ANTIBIOTIC MI43-37F11 SUBSTANCE

SUMMARY OF THE INVENTION

This invention relates to a new anticancer antibiotic and a process for the fermentative production of this new anticancer antibiotic.

More particularly, this invention relates to a new anticancer antibiotic, now nominated as MI43-37F11 substance. This invention also relates to a process for the fermentative production of the new anticancer antibiotic, MI43-37F11 substance. This invention further includes a pharmaceutical composition comprising MI43-37F11 substance as active ingredient, in combination with a carrier for the active ingredient.

This invention also relates to a pharmaceutical use of the new antibiotic, MI43-37F11 substance as an anticancer or cancerocidal agent or as an agent for enhancement of the production of interleukin-1 in vivo or as an agent for activation of macrophages in vivo in a mammalian.

BACKGROUND OF THE INVENTION

It is known that many of the known antibiotic substances which are produced by the cultivation of different kinds of microorganisms can exhibit an anticancer or antitumor activity. Up to date, some of the known anticancer antibiotic or antitumor antibiotic substances have extensively been used as a chemotherapeutic anticancer or antitumor agent and provide an important mean for therapeutic treatment of cancers or tumors in the clinic practice. However, many of the known anticancer antibiotic substances which have been used in the clinic practice can exhibit considerable toxicity to human body so that the practical use of them is greatly limited. In this sense, all the known anticancer antibiotics which have been used in the clinic practice are not necessarily a completely satisfactory anticancer agent or antitumor agent. Accordingly, there now remains an outstanding demand to discover and provide such novel substances that have a low toxicity to human but a high anticancer or antitumor activity and that can be effectively and safely used for the therapeutic treatment of a cancer or tumor in human patients. An object of this invention is to provide a new antibiotic substance which is useful as an anticancer agent or antitumor agent having the above-mentioned desirable properties. Another object of this invention is to provide a new anticancer antibiotic, now nominated as MI43-37F11 substance, which is utilizable as the anticancer or cancerocidal agent or as the antitumor agent having the above-mentioned desirable properties in the clinic practice. A further object of this invention is to provide a process for the fermentative production of the new anticancer antibiotic, MI43-37F11 substance. Still another objects of this invention will be clear from the following descriptions.

Thus, we, the present inventors, have made extensive researches in an attempt to discover and provide a new anticancer antibiotic substance, and we have now succeeded in obtaining a new anticancer antibiotic, now nominated as MI43-37F11 substance, and having the following formula [I]:

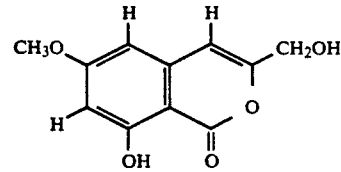

from the culture of a certain new microbial strain, and have found that this MI43-37F11 substance exhibits a highly useful anticancer activity without showing any observable toxicity to mammalian. We have now thus accomplished this invention.

DETAILED DESCRIPTION OF THE INVENTION

In a first aspect of this invention, therefore, there is provided a new antibiotic, MI43-37F11 substance which exhibits an anticancer activity and which is a compound having the following formula [I]:

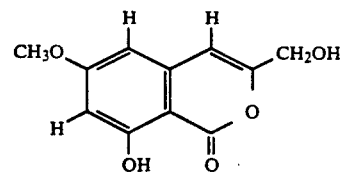

The new antibiotic, MI43-37F11 substance according to this invention is remarkedly characterized in that it can exhibit a high activity against Ehrlich carcinoma.

Physicochemical and biological properties of the antibiotic, MI43-37F11 substance according to this invention are described below.

(A) Physicochemical properties of the antibiotic MI43-37F11 substance (1) Appearance : Colorless needles.

(2) Molecular weight (as measured by FD mass spectrometry), m/z: 222.

(3) Elementary analysis : Found: C, 59.40%, H, 4.54%, O, 35.79%.

(4) Empirical formula : $C_{11}H_{10}O_5$.

(5) Specific optical rotation : $[\alpha]_D$ 0° C. (c 0.2, acetonitrile).

(6) Melting point : 148.5–149.5° C.

Figure 1:
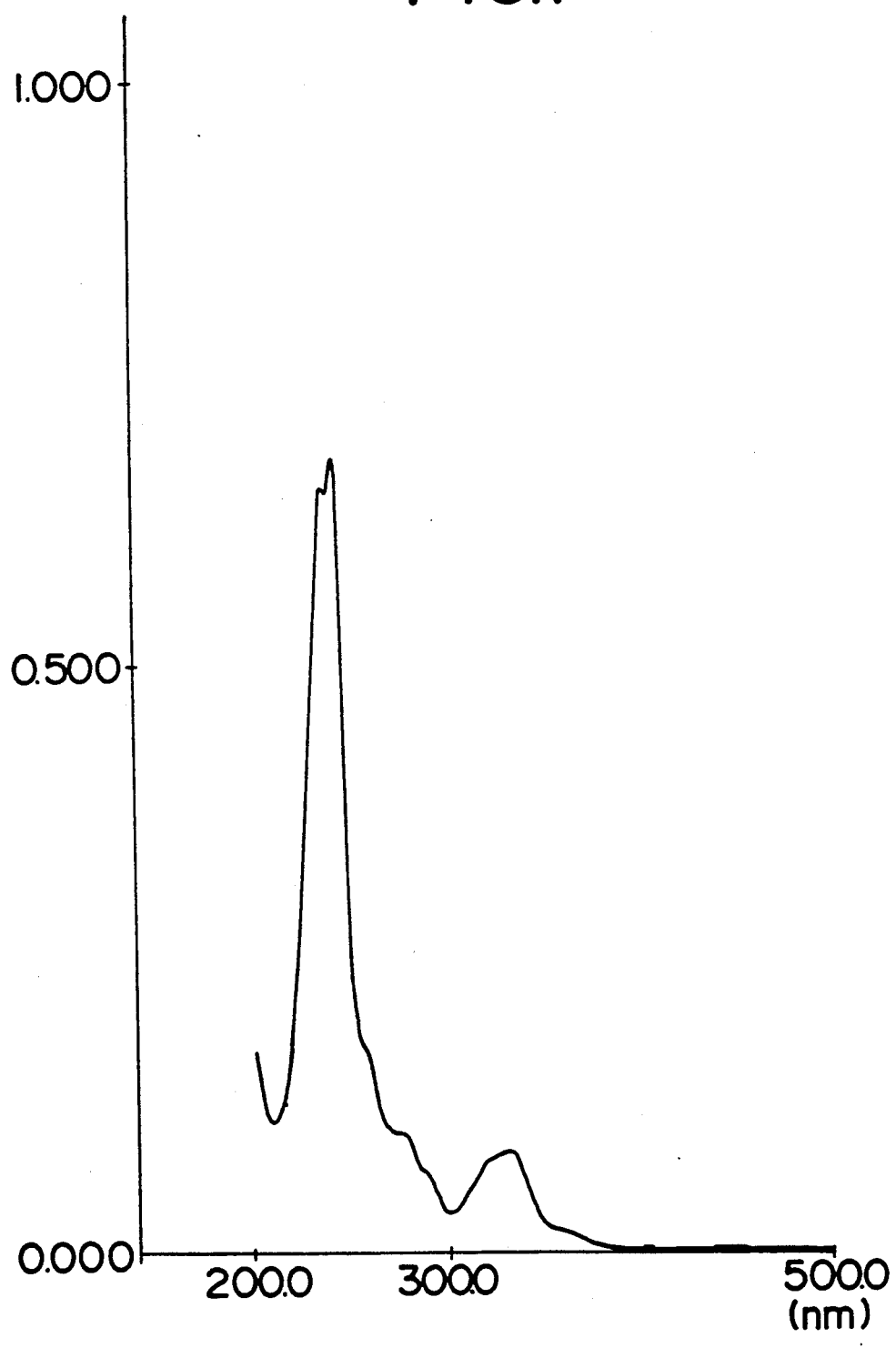

(7) Ultra-violet absorption spectrum (as shown in FIG. 1 of the accompanying drawings) :

λmax methanol 238 nm (4.63), 244 nm (4.65), 256 nm (sh, 4.05), 274 nm (sh, 3.82), 286 nm (sh, 3.67), 330 nm (3.78) (the numerial data given in the brackets are of the corresponding log s value)

Figure 2:
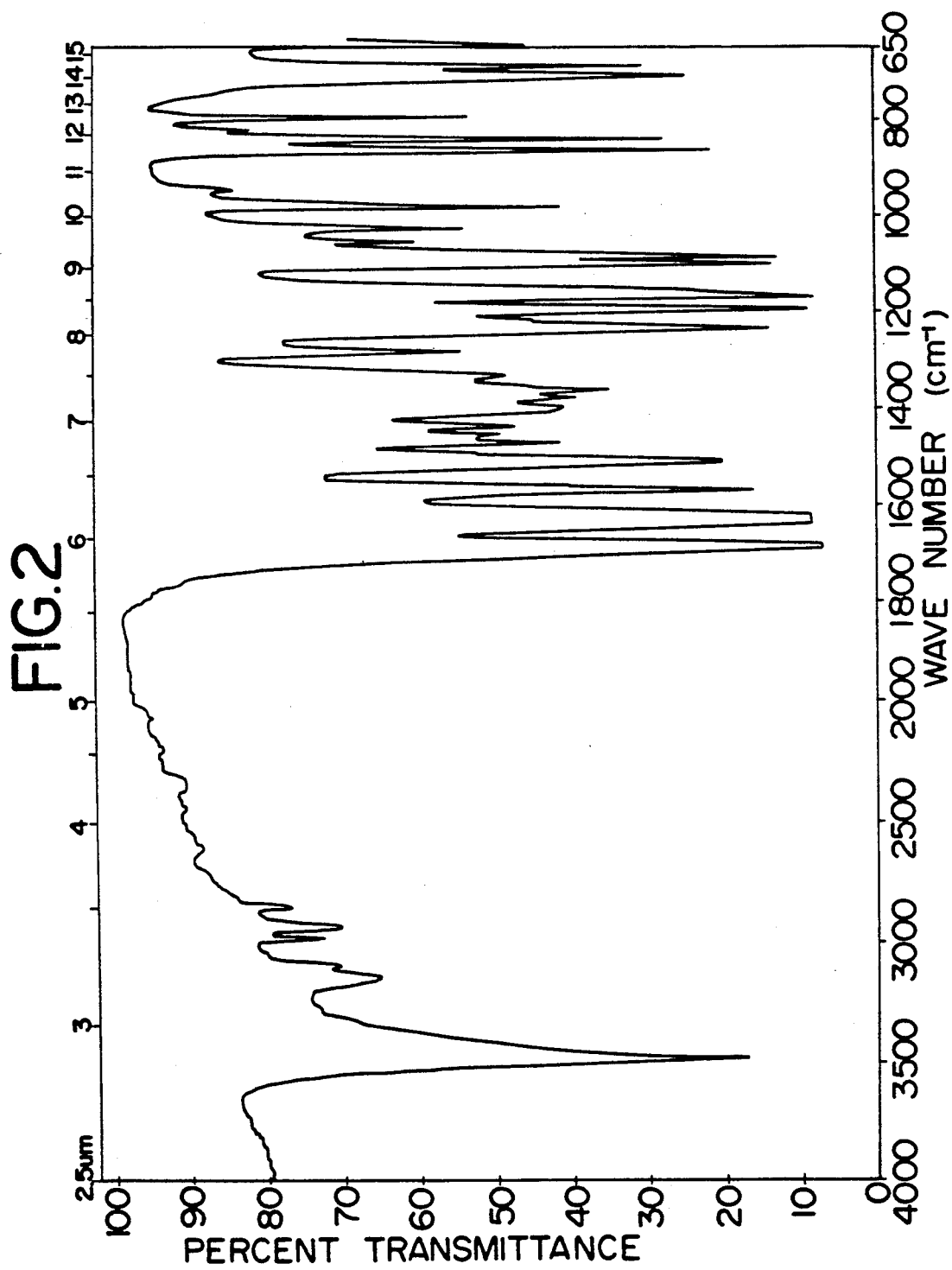

(8) Infrared absorption spectrum (as shown in FIG. 2 of the accompanying drawing) : characteristic peaks at 3480, 1680, 1630, 1570, 1510, 1230, 1190, 1170, 1100, 1090, 980, 860, 840, 710, 690 ($cm^{-1}$)

(9) Solubility : easily soluble in acetonitrile, soluble in methanol and chloroform, but hardly soluble in water and hexane.

Figure 3:
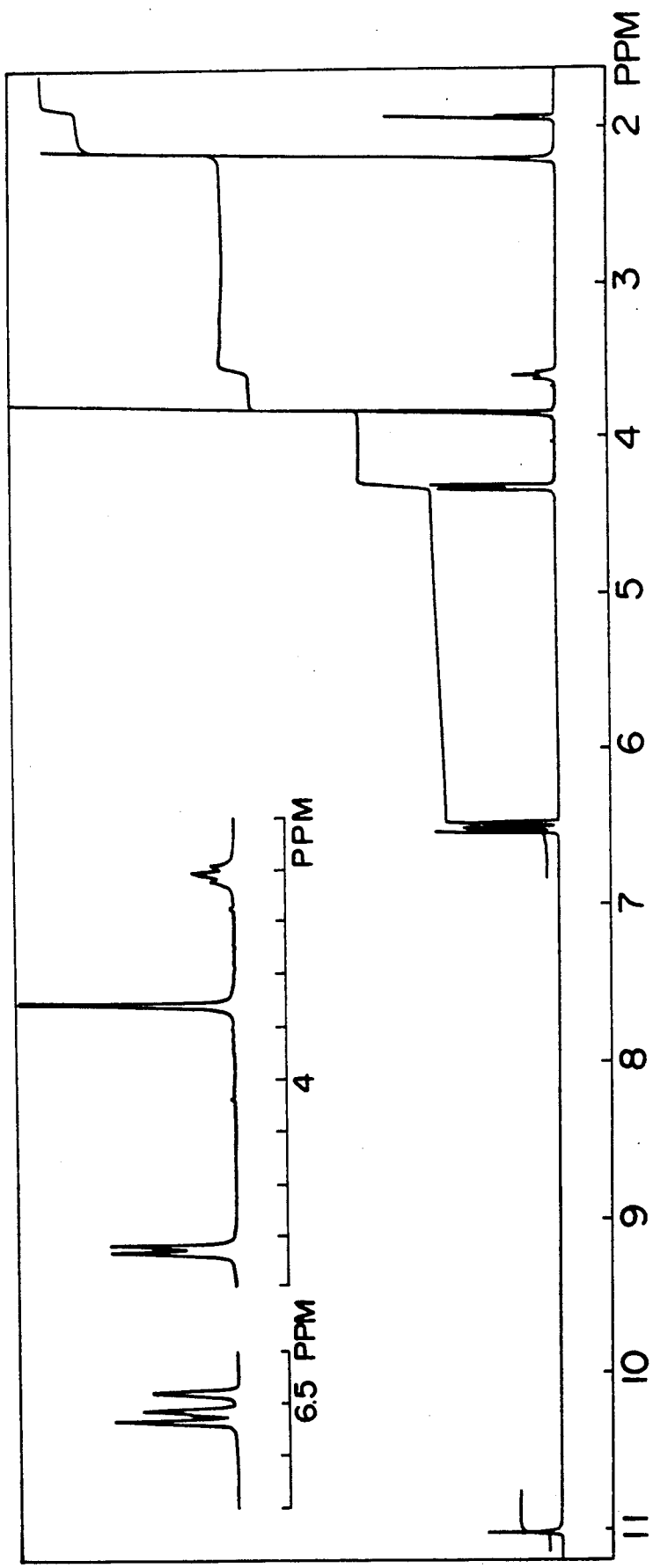

(10) Proton nuclear magnetic resonance absorption spectrum : $^1$H-NMR as measured in deutero-acetonitrile is shown in FIG. 3 of the accompanying drawings (Abscissa : ppm). Tetramethylsilane was used as the internal standard.

Besides, 13C-NMR of the MI43-37F11 substance as measured in deutero-acetonitrile is shown in Table 1 below.

TABLE 1

| 168.0 s | 167.0 s | 164.4 s |
|---|---|---|
| 157.9 s | 140.4 s | 104.2 d |
| 102.6 d | 101.5 d | 101.0 s |
| 61.1 t | 56.7 q | |

In Table 1, Note;
s: singlet
d: doublet
t: triplet
q: quartet

Tetramethylsilane was used as the internal standard.

With reference to the accompanying drawings: FIG. 1 is a UV absorption spectrum of the MI43-37F11 substance according to this invention: FIG. 2 is an IR absorption spectrum of the MI43-37F11 substance according to this invention : and FIG. 3 is a 1H-NMR absorption spectrum of the MI43-37F11 substance according to this invention.

Based on the various physico-chemical properties of the MI43-37F11 substance as described above, the determination of the chemical structure of the MI43-37F11 substance was made as follows. This substance shows a molecular ion peak at 222 (m/z) in the FD Mass Spectrometry. The result of the elementary analysis supports an empirical formula of $C_{11}H_{10}O_5$ for this substance. The ultra-violet absorption spectrum as shown in FIG. 1 and infrared absorption spectrum as shown in FIG. 2 reveal that the MI43-37F11 substance has an isocumarin skeleton. 1H-NMR spectrum as shown in FIG. 3 suggests the existence of the group

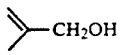

and the group

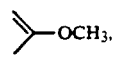

as well as the signals of three aromatic hydrogen atoms and the existence of one hydroxyl group which is forming the hydrogen-bond. 13C-NMR spectrum exhibits eleven signals as shown in the Table 1. The positions of the substituents CH2OH, OCH3 and OH on the isocumarin nucleus are decided by comparing with the spectra of Heteronuclear multiple bond connectivity (A. Bax et al, "J. Am. Soc", 108, 8056–8063 (1986)).

Through the examination of the above-mentioned different spectra of the MI43-37F11 substance, it has been decided that the MI43-37F11 substance has the chemical structure of the formula [I]as shown above. The antibiotic MI43-37F11 substance has also been confirmed to be a novel antibiotic as there is not reported any known substance which is coincident with the structure of the formula [I]shown above.

The antibiotic MI43-37F11 substance according to this invention is such a compound which is found at the first time to exhibit the anticancer activity, amongst the known isocumarins. Besides, owing to its low toxicity to mammalian, the antibiotic MI43-37F11 substance is expectable to be an anticancer antibiotic useful in the chemotherapeutic treatment of cancer-bearing patients.

By the way, we have been aware of that Japanese patent application publication "Kokai" No. 71076/78 (published on 24 June 1978) discloses 3-hydroxymethyl-6, 7-dimethoxy-8-hydroxyisocumarin of formula

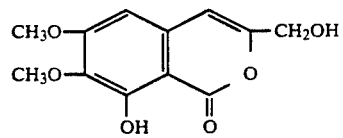

and 3-hydroxymethyl-6,8-dihydroxy-7-methoxyisocumarin having an inhibitory activity to cyclic adenosine monophosphate (CAMP) phosphodiesterase. In said Japanese patent application publication, there is described that the isocumarin derivatives as disclosed therein would be expectable to exhibit an anticancer activity, a hypotensive activity, an anti-inflammatory activity and anti-allergic activity etc., but there is not given at all any experimental data for showing that the isocumarin derivatives as disclosed therein actually can exhibit any anticancer activity.

(B) Biological properties of the antibiotic MI43-37F11 substance (1) Antitumor activity of MI43-37F11 substance to inhibit the proliferation of various sorts of experimental tumor cells and human cancer cells.

A cell suspension containing cells of mouse Leukemia L1210, mouse Leukemia P388, mouse Leukemia EL4, mouse IMC carcinoma or human lung cancer LX-1 cells in a culture medium containing 10% calf serum at a cell density of 1 x 105 cells/ml was prepared, and 200 μl-portion of the cell suspension so prepared was placed in a microplate and then added with a solution of MI43-37F11 substance at varying concentrations (dissolved in a mixture of water and dimethylsulfoxide (95:5)). The cell suspension containing the test compound added was subsequently incubated at 37° C for 2 days (but 5 days for the LX-1 cells).

After the incubation, the number of the cells of the L1210 cells, P388 cells, the EL4 cells and the IMC carcinoma cells in the treated groups was counted by means of Coulter-counter. The control group (untreated) of the cell suspension to which the test compound was not added was incubated in the same way as above and then the number of the cells was similarly counted.

Rate (%) of inhibition of the cell proliferation of the treated group against that of the control group (untreated) was evaluated.

With the human lung cancer LX-1 cell, however, the incubated cell suspension of LX-1 cells was added with 10 μl of a solution containing 5 mg/m( of MTT (namely, 3-(4,5-dimethylthiazol-2-yl)-2,5-diphenyl tetrazolium bromide), followed by further incubation at 37° C. for 4 hours. After the completed incubation, the supernatant liquor (100 μl) was removed from the incubated cell suspension and the resultant residual suspension containing the LX-1 cells was added with 150 μl of a mixture of isopropanol and 1N-HC( (25:1). The resulting mixture was evaluated for its absorption of light ray at 540 nm. Rate (%) of inhibition of the proliferation of the LX-1 cells in the treated group against that of the control group (untreated) was evaluated in terms of the evaluated values of the absorption of light ray at 540 nm.

From the values of the rate (%) of inhibition as evaluated as above, there were estimated the values of IC$_{50}$ (μg/m;) of MI43-37F11 substance of this invention, that is, the concentration of MI43-37F11 substance which can give 50% inhibition of the proliferation of the various cancer cells tested. The test results are summarized in Table 2 below.

TABLE 2

| Tested cells | IC$_{50}$ Value (μg/ml) |
| --- | --- |
| Mouse leukemia L1210 | 50 |
| Mouse leukemia P388 | 50 |
| Mouse leukemia EL4 | 52 |
| Mouse IMC carcinoma | 72 |
| Human lung cancer LX-1 | 100 |

(2) Antitumor effect of the antibiotic MI43-37F11 substance on Ehrlich carcinoma was estimated by the following procedures (a) Experiments for therapeutic treatment of Ehrlich carcinoma-bearing mice were conducted by intraperitoneal injection of the antibiotic MI43-37F11 substance. Thus, a cell suspension of Ehrlich ascites carcinoma cells was subcutaneously inoculated at the abdominal region of ICR mice (female, 6-week old, 4 mice in each treated group) so that the number of the carcinoma cells as subcutaneously transplanted was $2 \times 10^6$ cells per mouse. After the transplantation of the carcinoma cells, the antibiotic MI43-37F11 substance was administered by intraperitoneal injection to the mice having the transplanted and firmly grown carcinoma cells, according to the following schedule of administration. Namely, MI43-37F11 substance was administered at a dosage of 10 mg/kg or 2.5 mg/kg or 0.625 mg/kg only once on the 7th day after the transplantation of the cells, or alternatively MI43-37F11 substance was administered at a dosage of 2.5 mg/kg or 1.25 mg/kg or 0.625 mg/kg, totally five times but every other day from the 7th day to the 14th day after the transplantation of the carcinoma cells. The administration of MI43-37F11 substance was not made but intraperitoneal injection of physiological saline was made in the mice of the control group (untreated) (8 mice in each control group).

On the 15th day after the transplantation of the carcinoma cells, the mass of the tumor (carcinoma) was surgically removed out of each mouse and weighed. The rate of the reduction in the weight of the tumor (carcinoma) obtained from the group of mice treated with MI43-37F11 substance was evaluated in term of the rate (%) of inhibition, with such an assumption that the weight of the tumor obtained from the control group of mice was amounting to 100. In other words, the rate (%) of inhibition to the growth of Ehrlich carcinoma was calculated according to the following equation $$\text{Rate (\%) of Inhibition} = \frac{(C - T)}{C} \times 100$$

where C means the weight of the tumor in the control group of mice (untreated) and T means the weight of the tumor of the treated group of mice.

The test results obtained are shown in Table 3 below.

TABLE 3

| Dosage of MI43-37F11 Substance (mg/kg/day) | Rate (%) of Inhibition Schedule of administration | |
| --- | --- | --- |
| | 7th day (only once) | 7th day to 14th day (every second day, totally 5 times) |
| 10 | 59 | — |
| 2.5 | 51 | 60 |
| 1.25 | — | 67 |
| 0.625 | 12 | 30 |

(b) Another experiments for therapeutic treatment of Ehrlich carcinoma-bearing mice were conducted by oral administration of MI43-37F11 substance. Thus, the cell suspension of Ehrlich ascites carcinoma cells was subcutaneously inoculated at the abdominal region of ICR mice (female, 6-week old, 5 mice in each treated group) so that the number of the carcinoma cells as subcutaneously implanted was $2 \times 10^6$ cells per mouse. The MI43-37F11 substance was orally administered to the mice of the treated group at a dosage of 6.3 mg/kg, 12.5 mg/kg, 25 mg/kg, 50 kg/mg or 100 mg/kg once a day during the consecutive 9 days from the 1st day to the 9th day after the implantation of the carcinoma cells. On the 14th day after the implantation of the carcinoma cells, the mass of the tumor (carcinoma) was surgically removed out of each mouse and weighed. The weight of the tumor obtained from the treated group of mice was compared with the weight of the tumor obtained from the control group of mice (untreated), by calculating the rate (%) of inhibition according to the same equation as above.

The test results obtained are shown in Table 4 below.

TABLE 4

| Dosage of MI43-37F11 substance (mg/kg/day) | Weight of tumor (mg ± S.D.) | Rate (%) of Inhibition |
| --- | --- | --- |
| 0 | 1,084 ± 256 | — |
| 6.3 | 586 ± 282* | 45 |
| 12.5 | 391 ± 266** | 63 |
| 25.0 | 280 ± 152*** | 74 |
| 50.0 | 485 ± 123** | 55 |
| 100.0 | 566 ± 421** | 47 |

*$P < 0.001$, $P < 0.01$, *$P < 0.05$ (3) Experiments for estimation. of the activity of MI43-37F11 substance to activate peritoneal macrophages were conducted by the following procedure. Thus, one day before the harvest of the peritoneal macrophages, the antibiotic MI43-37F11 substance was intraperitoneally administered to CDF$_1$ mice (8-week old, female, 3 mice in each group) at a dosage of 50 mg/kg, 12.5 mg/kg or 3.125 mg/kg. One day after the administration, the macrophages were harvested from the peritoneal cavity of the treated mice and placed into a culture medium present in a plastic dish (Falcone, No. 3002, 60 x 15 cm, a product of Decton Dikinson & Company) at the cell concentration of $1 \times 10^6$ cells/m(, followed by incubation of the macrophages. The incubated medium containing the macrophages was then added with 100 ng/ml of phorbol myristate acetate to elicit the macrophages for their production of $O_2-$. The amount of $O_2-$ was determined by reductive reaction with cytochrome C. The control group of mice (untreated) received only intraperitoneal injection of physiological saline in place of the administration of MI43-37F11 substance before the harvest of the peritoneal macrophages was done. Assumed that the amount of $O_2-$ as produced and liberated by the peritoneal macrophages which were harvested from the mice of the control group was amounting to 100, the rate of increase in the amount of $O_2-$ as produced by the peritoneal macrophages of the mice of the treated group was evaluated. In other words, the rate (%) of increase in the production of $O_2-$ by the peritoneal macrophages of the mice of the treated group was calculated according to the following equation;

$$\text{Rate (\%) of increase in the production of } O_2^- = \frac{(T-C)}{C} \times 100$$

where T means the amount of $O_2-$ produced by the peritoneal macrophages of the mice of the treated group and C means the amount of $O_2-$ produced by the peritoneal macrophages of the control group (untreated).

The test results obtained are summarized in Table 5 below.

TABLE 5

| Dosage of MI43-37F11 substance (mg/kg) | Rate (%) of increase in production of $O_2^-$ |
| --- | --- |
| 50 | 255 |
| 12.5 | 127 |
| 3.125 | 105 |

(4) Experiments for estimation of the effect of the antibiotic MI43-37F11 substance on phagocytosis of the peritoneal macrophages were conducted by the following procedure. Thus, 3 days and one day before the harvest of the peritoneal macrophages, MI43-37F11 substance was intraperitoneally administered to CDF$_1$ mice (female, 8-weeks old, 3 mice) at a dosage of 50 mg/kg, 5 mg/kg or 0.5 mg/kg. One day after the administration of MI43-37F11 substance, the peritoneal macrophages were harvested from the peritoneal cavity of the mice of the treated group of mice and then inoculated into a culture medium present in a plastic dish (Falcone) at the cell density of $5 \times 10^5$ cells/m(, followed by incubation of the macrophages. The incubated medium containing the macrophages was then added with $7.5 \times 10^6$ cells/ml of heat-treated yeast cells, followed by further incubation for a time. The macrophages were then fixed by addition of methanol and stained by Giemsa staining method. The number of the yeast cells which received the phagocytosis by 400 macrophages was counted. The control group of mice (untreated) received only intraperitoneal injection of physiological saline in place of the administration of MI43-37F11 substance, before the harvest of the peritoneal macrophages was done. Assumed that the number of the yeast cells which had received the phagocytosis by 400 macrophages as harvested from the mice of the control group was amounting to 100, the rate of increase in the phagocytic action of the peritoneal macrophages as harvested from the treated group of mice was evaluated. In other words, the rate (%) of increase in the phagocytic action of the peritoneal macrophages of the mice of the treated group was calculated according to the following equation:

$$\text{Rate (\%) of increase in the phagocytic action} = \frac{(T-C)}{C} \times 100$$

where T means the mumber of yeast cells having received the phagocytosis by 400 macrophages which were harvested from the treated group of mice, and C means the number of yeast cells having received the phagocytosis by 400 macrophages which were harvested from the control group of mice (untreated).

The test results are shown in Table 6 below.

TABLE 6

| Dosage of MI43-37F11 substance (mg/kg) | Rate (%) of Increase in phagocytic action of peritoneal macrophages |
| --- | --- |
| 50 | 144 |
| 5 | 80 |
| 0.5 | 102 |

(5) Experiments for estimation of the activity of the antibiotic MI43-37F11 substance to enhance the production of interleukin-1 in vivo was conducted by the following procedure. Thus, MI43-37F11 substance was orally administered to CDF$_1$ mice (female, 6-week old) B at a dosage of 25 mg/kg. One day, 3 days, 5 days and days after the administration, peritoneal exudate cells (PEC) and spleen cells were respectively harvested from the mice of the treated group. The peritoneal exudate cells and spleen cells as harvested were independently divided into two classes, namely the class of the adherent cell which was adherent in its nature to the wall of a plastic dish and the class of the non-adherent cell. The whole peritoneal exudate cells (PEC), the adherent cells of PEC and the adherent cells of the spleen cell were separately suspended into aliquots of a culture medium to give a cell concentrations of $1 \times 10^6$ cells/well, $2 \times 10^6$ cells/well and $2.5 \times 10^6$ cells/well, respectively. After the incubation for 24 hours, the supernatants were collected by filtration of the incubated culture media and then assayed for their activity of interleukin-1 (IL-1) according to the method of Jonathan K. et al (see "Lymphokine Research" 3 (4), 175-182, (1984)). Namely, 100 μl of each supernatant obtained as above and Concanavalin A (to a final concentration of 2.5 μg/ml) were added to 100 μl of a cell suspension containing 1 x 105 cells/m( of D10.G4.1. cells which will proliferate in the presence of Concanavalin A plus interleukin-1 when the latter compounds are given. The resulting mixture was then incubated for 48 hours and then added with $^3$H-thymidine ($^3$H-TdR), followed by further incubation for 16 hours. After this, the rate of uptake of $^3$H-TdR by the D10.G4.1. cells was determined in term of the radio-activity unit of c.p.m. The rate of uptake of $^3$H-TdR in the control group of mice (untreated) was also determined in the same manner as above.

The test results obtained are summarized in Table 7 below.

TABLE 7

| Days after oral administration of MI43-37F11 substance (25 mg/kg) | Uptake of $^3$H-TdR (c.p.m.) | | | | | |
| --- | --- | --- | --- | --- | --- | --- |
| | Whole peritoneal exudate cells (PEC) | | Adherent cell in PEC | | Adherent cell in spleen cells | |
| | c.p.m. ± S.D. | T/C % | c.p.m. ± S.D. | T/C % | c.p.m. ± S.D. | T/C % |
| Control | 7166 ± 752 | 100 | 10561 ± 1241 | 100 | 2091 ± 481 | 100 |
| 1 day | 4393 ± 397** | 61.3 | 17510 ± 810** | 165.8 | 1741 ± 352 | 83.3 |

TABLE 7-continued

| Days after oral administration of MI43-37F11 substance (25 mg/kg) | Uptake of $^3$H-TdR (c.p.m.) | | | | | |
|---|---|---|---|---|---|---|
| | Whole peritoneal exudate cells (PEC) | | Adherent cell in PEC | | Adherent cell in spleen cells | |
| | c.p.m. ± S.D. | T/C % | c.p.m. ± S.D. | T/C % | c.p.m. ± S.D. | T/C % |
| 3 days | 5988 ± 602 | 83.6 | 13912 ± 1367** | 131.7 | 4868 ± 497** | 232.8 |
| 5 days | 28072 ± 1174*** | 391.7 | 26759 ± 3601*** | 253.4 | 2140 ± 121 | 102.3 |
| 7 days | 3906 ± 465** | 54.5 | 17639 ± 2699* | 167.0 | 2385 ± 134 | 114.1 |

In a second aspect of this invention, there is provided a process for the production of the anti-cancer antibiotic, MI43-37F11 substance having the formula [I] as described hereinbefore, which comprises culturing an MI43-37F11 substance-producing strain of the genus Streptoverticillium in a culture medium containing assimilable carbon sources and assimilable nitrogen sources, until a substantial amount of MI43-37F11 substance is produced and accumulated in the culture, and then recovering MI43-37F11 substance having the above formula [I] from the resulting culture.

One typical example of the MI43-37F11 substance-producing strain available in the process of the second aspect of this invention is a new strain designated as MI43-37F11 strain, which belongs to the genus Streptoverticillum, and which was isolated by us from a soil sample collected in Midori-ku, Yokohama City, Kanagawa Prefecture, Japan. This MI43-37F11 strain has the following microbiological properties.

1. Morphological observations

Microscopic observation shows that the MI43-37F11 strain has branched substrate mycelia, from which aerial hyphae develop with formation of whirls. It is observed that a chain of more than 10 spores is formed at the tip of the aerial hyphae. No spiral-formation is observed. Spores are measuring about 0.7–0.8 by 1.1–1.3 microns in size annd have smooth surface.

2. Growth charcteristics on various culture media

The standard given in each of the brackets [ ] for the description of color is according to "Color Harmony Manual" of Container Corporation of America.

(1) Sucrose-nitrate-agar medium (cultured at 27° C.)

White aerial hyphae are thinnly formed on the colorless growth. No soluble pigment is observed.

(2) Glucose-asparagine-agar medium (cultured at 27° C.)

Aerial hyphae of yellow-tinged white [1½db, Parchmeat] in color are thinnly formed on the growth of colorless to pale yellow [2ea, Lt Wheat] to pale yellowish brown [2 gc, Bamboo] in color. White cottonyl aerial hyphae are also partly formed. No soluble pigment is observed.

(3) Glycerine-asparagine-agar medium (ISP-medium 5, cultured at 27° C.)

10 Colorless aerial hyphae are formed on the growth of colorless to pale yellowish brown [2 ie, Lt Mustard Tan] in color. The soluble pigment is tinged with brown.

(4) Starch-inorganic salt-agar medium (ISP-medium 4, cultured at 27° C.)

Aerial hyphae of yellowish white [11½ca, Cream] to bright olive gray [1½ ge, Lt Olive Gray] in color are formed on the growth of colorless to pale yellowish brown [2 le, Mustard - 2 ne, Mustard Gold] in color. No soluble pigment is observed.

(5) Tyrosine-agar medium (ISP-medium 7, cultured at 27° C.)

Aerial hyphae of white to brownish white [3 ba, Pearl—2 cb, Ivory Tint] in color are formed on the growth of pale yellowish brown [2 ie, Lt Mustard Tan] to bright grayish brown [2 lg, Mustard Tan] in color. No soluble pigment is observed.

(6) Nutrient agar medium (cultured at 27° C.)

White aerial hyphae are thinnly formed on the growth of colorless to pale yellowish brown [2 ie, Lt Mustard Tan] in color. Black-tinged soluble pigment is slightly produced.

(7) Yeast-malt agar medium (ISP-medium 2, cultured at 27° C.)

Aerial hyphae of white to brownish white [3 ba, Pearl] in color are formed on the wrinkled growth of colorless to pale yellowish brown [2 ic, Honey Gold —3 ic, Lt Amber] in color. No soluble pigment is observed.

(8) Oatmeal agar medium (ISP-medium 3, cultured at 27° C.)

Aerial hyphae of white to yellowish white are thinnly formed on the growth of colorless to pale yellow [2 ea, Lt Wheat - 2 ca, Lt Ivory] in color. No soluble pigment is observed.

(9) Glycerin-nitrate-agar medium (cultured at 27° C.)

Aerial hyphae of white to yellowish white [1½ db, Parchment] are thinly formed on the growth of colorless to pale yellow [2 ca, Lt Ivory] in color. No soluble pigment is observed.

(10) Starch agar medium (cultured at 27° C.)

Aerial hyphae of white to yellowish white [2 ca, Lt Ivory] are formed on the growth of colorless to pale yellow [2 ea, Lt Wheat] to pale yellowish brown [1½ ic, Lt Antique Gold] in color. No soluble pigment is observed.

(11) Calcium malate-agar medium (cultured at 27° C.)

White aerial hyphae are slightly formed on the colorless and very poor growth. No soluble pigment is observed.

(12) Cellulose (synthetic test solution containing filter paper pieces, cultured at 27° C.)

The growth is colorless and aerial hyphae are not formed thereon. No soluble pigment is observed.

(13) Gelatin stab

In a 15% simple gelatin culture medium (cultured at 20° C.), the growth is colorless but no aerial hyphae are formed, and soluble pigment of pale yellowish brown is observed. In glucose-peptone-gelatin culture medium (cultured at 27° C.), the growth is colorless but no aerial hyphae are formed, and soluble pigment of slightly brownish color is observed.

(14) Skimmed milk (cultured at 37° C.)

The growth is cololess to pale brown and no aerial hyphae are formed. Soluble pigment of slightly yellowish to brownish color is observed.

3. Physiological properties (1) Temperature range for the growing

In the tests which were conducted using a starch-inorganic salt-agar medium (ISP-medium 4, BACTO-INORGANIC-SALTS STARCH AGAR) and incubating the MI43-37F11 strain at different temperatures of 20° C., 24° C., 27° C., 30° C., 37° C. and 50° C., the MI43-37F11 strain grows at all the temperatures tested, but not at 50° C. Optimum temperature for good growth appears to be in the vicinity of 27° C.

(2) Liquefaction of gelatin (in 15% simple gelatin medium, cultured at 20° C.; and in glucose-peptone-gelatin medium, cultured at 27° C.)

Liquefaction started about at the third day of the incubation both in the 15% simple gelatin medium and in the glucose-peptone-gelatin medium. The grade of liquefaction is medium to rather strong.

(3) Hydrolysis of starch (starch-inorganic salt agar medium and starch-agar medium, each cultured at 27° C.)

Hydrolysis started about at the third day of the incubation both in the starch-inorganic salt agar medium and in the starch agar medium, where the grade of hydrolysis is rather strong.

(4) Coagulation and peptonization of skimmed milk (skimmed milk, cultured at 37° C.)

Coagulation was exhibited about at the second day of the incubation and then was completed at the third day of the incubation, and thereafter immediately the peptonization started. The peptonization proceeded slowly and was not completed even after 3 weeks of the incubation.

(5) Formation of melanoid pigment (Trypton-yeast broth, ISP-medium 1; peptone-yeast-iron agar medium, ISP-medium 6; tyrosine-agar medium, ISP-medium 7; each cultured at 27° C.)

The melanoid formation was positive in the peptone-yeast-iron medium and was apparently positive in the tryptone-yeast-broth but was negative in the tyrosine-agar medium.

(6) Utilization of various carbon sources (Pridham-Gottlieb agar medium, ISP-medium 9, cultured at 27° C.)

Glucose, fructose and inositol are utilizable for the growth. But, L-arabinose, D-xylose, sucrose, rhamnose, raffinose, D-mannitol and lactose are not utilizable.

(7) Liquefaction of calcium malate (calcium malate agar medium, cultured at 27° C.)

Liquefaction of calcium malate in the calcium malate agar was negative.

(8) Reduction of nitrate (aqueous peptone solution containing 0.1% potassium nitrate, ISP-medium 8, cultured at 27° C.)

The reduction was rather faintly positive.

(9) Decomposition of cellulose (synthetic test solution containing filter paper pieces, cultured at 27° C.)

The decomposition of cellulose was negative.

Summarizing the microbiological properties described above, the MI43-37F11 strain is morphologically characterized in that the aerial hyphae have whirls, but the formation of spirals is not observed. The spore surface is smooth. The aerial hyphae of white to brown tinged white, or yellowish white, or occasionally bright olive gray in color are formed on the growth of colorless to pale yellowish brown color, in various culture media. Soluble pigment is not produced, or occasionally soluble pigment of brown tinged color is observed. The formation of the melanoid pigment is negative in the tyrosine-agar medium, but is positive in the tryptone-yeast broth and in the peptone-yeast-iron agar medium. The grade of the protein-decomposing activity is medium to rather strong, and the grade of the starch-hydrolyzing activity is rather strong, too. 2,6-Diaminopimelic acid present in the cell wall is of the LL-type.

In view of the microbiological properties described above, we have judged that the MI43-37F11 strain belongs to the genus *Streptoverticillium*.

When searching analogous known species with reference to the properties of the MI43-37F11 strain, *Streptoverticillium eurocidicum* [Literature 1: "International Journal of Systematic Bacteriology", Vol. 22, p. 293 (1972) ; Literature 2 : ditto, Vol. 30, p. 408 (1980) ; Literature 3 : "The Journal of Antibiotics, Ser. A.", Vol. 7, p. 98 (1954)]and *Streptoverticillium albireticuli* [Literature 1 : "International Journal of Systematic Bacteriology", Vol. 18, p. 80 (1968) ; Literature 2 : ditto, Vol. 30, p. 407 (1980)]appear to resemble to the MI43-37F11 strain.

Then, our study was made for the comprisons between the properties of the MI43-37F11 strain, and the properties of *Streptoverticillium eurocidium* and of *Streptoverticillium albireticuli* as described in the above literatures. The results of these comprisons are summarized in the Table 8 below.

TABLE 8

| | MI43-37F11 | *Streptoverticillium eurocidicum* IMC S-0770(ISP5604) | *Streptoverticillium albireticuli* IMC S-0222(ISP5051) |
|---|---|---|---|
| Nature of aerial hyphae | Formation of whirls | Formation of whirls | Formation of whirls |
| Spore surface | Smooth | Smooth | Smooth |
| Color of aerial hyphae | White to yellow tinged white brownish white, or bright olive gray | White to yellow tinged white brownish white, or bright olive gray | White to yellow tinged white |
| Color of growth | Colorless to pale yellowish | Colorless to pale yellowish | Colorless to pale yellowish |

TABLE 8-continued

|  | MI43-37F11 | Streptoverticillium eurocidicum IMC S-0770(ISP5604) | | Streptoverticillium albireticuli IMC S-0222(ISP5051) | |
| --- | --- | --- | --- | --- | --- |
| Soluble pigment | brown | brown | | brown | |
| Formation of melanoids | — | — | | — | |
|  |  | Lit.*1 | Lit.*2 | Lit.*3 | Lit.*4 |
| In ISP-medium 1 | (+) | + | + | + | No description |
| In ISP-medium 6 | + | + | + | + | + |
| In ISP-medium 7 | ∓ | ∓ | — | ? | + | + |
| Hydrolysis of starch | + + + | + + + | | + + + | + + + |
| Coagulation of skimmed milk | + + + | + + + | | — | + + + |
| Peptonization of skimmed milk | + | (+) | | — | ∓ | slow |
| Gelatin Liquefaction |  |  |  |  |  |
| In 15% simple gelatin medium | + + | ∓ | | — | (+) slow | slow |
| In glucose-peptone-gelatin medium | + + | + | | | + + |  |
| Reduction of nitrate | (+) | + | | — | + | + |
| Carbon source utilization* |  |  |  |  |  |
| D-glucose | + | + | + | + | + |
| L-arabinose | — | — | — | — | — |
| D-xylose | — | — | — | — | — |
| D-fructose | (+) | (+) | + | ± | ? |
| Sucrose | — | — | — | — | — |
| Inositol | + | + | + | + | + |
| Rhamnose | — | — | — | — | — |
| Raffinose | — | — | — | — | — |
| D-mannitol | — | — | — | — | — |
| Lactose | — | — | | — |  |

Note:
In Table 8, the symbol "∓" means "possibly (−)", "?" means "doubtfully" and "(+)" means "possibly +".
*Particularly for carbon source utilization, the symbol "+" means "utilizable", "(+)" means "possibly utilizable"; "±" means "doubtfully either "+" or "−", "?" means "variable", and "−" means "not utilizable".
Literature*1 "International Journal of Systematic Bacteriology", Vol. 22, p. 293 (1972)
Literature*2 "The Journal of Antibiotics Ser. A", Vol. 7, p. 98 (1954)
Literature*3 "International Journal of Systematic Bacteriology", Vol. 18, p. 80 (1968)
Literature*4 S. A. Waksman; "The Actinomycetes", Vol. 2, p. 169 (1961).

As can be seen from Table 8 above, the MI43-37F11 strain closely resembles both to *Streptoverticillum eurocidicum* and *Streptoverticillium albireticuli.* However, in view of the bright olive gray color of the aerial hyphae, the probably "negative" formation of melanoid pigment in the ISP-medium 7, probable utilization of D-fructose and other properties of the MI43-37F11 strain, it is judged that the MI43-37F11 strain is most closely analogous to *Streptoverticillium eurocidicum.* Thus, the MI43-37F11 strain has now been identified as *Streptoverticillium eurocidicum* MI43-37F11.

The strain MI43-37F11 has been deposited in the Japanese depository "Fermentation Research Institute", Agency of Industrial Science and Technology (located at Tsukuba-City, Ibaraki Prefecture, Japan), since Jan. 27, 1989 under the deposit number "FERM P-10513" and now deposited under the deposit number "FERM BP-2783" in terms of the Budapest Treaty.

In carrying out the process for the production of the anticancer antibiotic MI43-37F11 substance according to the second aspect of this invention, an MI43-37F11 substance-producing strain belonging to the genus *Streptoverticillium* is cultivated by a known and ordinary method for the cultivation of microorganisms of Actinomyces. Thus, an amount of the MI43-37F11 substance-producing strain is inoculated to a suitable culture medium comprising assmilable carbon and nitrogen sources and is then incubated under aerobic conditions, preferably under submerged aerobic conditions, so that the MI43-37F11 substance is produced and accumulated in the culture broth.

The culture medium used for the cultivation may contain corbon sources, nitrogen sources and inorganic salt, etc., which are customarily used for the cultivation of Actinomyces. The nitrogen sources include those commercially available known materials such as peptone, meat extract, corn steep liquor, cotton seed meal, peanut powder, soybean powder, yeast extract, NZ-amine, casein-hydrolysate, sodium nitrate, ammonium nitrate and ammonium sulfate. The carbon sources include those commercially available known materials, for example, carbohydrate such as glycerin, starch, glucose, galactose, mannose and mollasses, and fats and oils. The inorganic salts may include sodium chloride, phosphates, calcium carbonate, magnesium sulfate etc.

The productive culture medium which may be used for commercial production of MI43-37F11 substance may contain a slight amount of one or more inorganic salts, and also may contain as anti-foaming agent animal oils, vegetable oils and mineral oils. Further, any other organic and inorganic materials which are known as the material useful for potentiation of the microorganisms and useful for enhanced production of MI43-37F11 substance may also be advantageously employed as the additive in the culture medium.

The cultivation of the MI43-37F11 strain for the commercial production of MI43-37F11 substance may be conducted under submerged, aerobic conditions and the cultivation temperature may be in a range of the temperature where the MI43-37F11 substance-producing strain can grow and produce a substantial amount of the MI43-37F11 substance, usually in a range of from 27° C. to 37° C. The other conditions for the cultivation may be selected, depending on and, according to the microbiological and physiological properties of the MI43-37F11 substance-producing strains.

The recovery of the MI43-37F11 substance from the culture of the MI43-37F11 substance-producing strain may be achieved in the following manner. The antibiotic MI43-37F11 is mainly accumulated in the liquid phase of the culture broth. Thus, the culture broth obtained is filtered, and the broth filtrate is adjusted to faintly acidic pH and extracted with a water-immiscible organic solvent such as ethyl acetate. In addition to the extraction method described above, any conventional methods for isolation of oleophilic substances, namely adsorption chromatography, gel-filtration chromatography, high performance liquid chromatography, and a combination thereof may also advantageously be employed for the isolation and purification of the MI43-37F11 substance.

This invention also includes use of the MI43-37F11 substance in a pharmaceutical composition.

On the basis of such useful biological properties of the MI43-37F11 substance as given above, a third aspect of this invention is a pharmaceutical composition comprising as active ingredient the antibiotic, MI43-37 F11 substance having formula (I) above, in combination with a pharmaceutically acceptable carrier or carriers for the active ingredient. The pharmaceutical composition according to this invention is effective and useful as carcinostatic or antitumor agent for mammalian animals, including man.

The pharmaceutical composition according to this invention may be formulated in a conventional manner into any convenient form of medicinal preparations for oral, intraperitoneal or parenteral administration such as, for example, injections, tablets, capsules, granules, syrups, suppositories and ointments. As pharmaceutically acceptable carriers, there may be used any of known, conventional ones as desired. The nature and composition of carreirs to be used may vary depending on the route and manner of administration and include organic and inorganic, solid and liquid, usually inert carriers and excipients known and available for pharmaceutical purposes. Some concrete examples of such carriers are crystalline cellulose, gelatin, lactose, starch, magnesium stearate, talc, vegetable and animal fats and oils, gums and polyalkylene glycols among others. The concentration of the active carcinostatic or antitumor ingredient, MI43-37F11 substance, in the pharmaceutical composition of this invention may vary from 0.2 to 100% by weight, preferably from 1 to 90% by weight, based on the total weight of the composition. If desired, the pharmaceutical composition of this invention may contain, in addition to the MI43-37F11 substance, one or more other pharmacologically active ingredients including those having carcinostatic, antitumor and other pharmacological activities.

The pharmaceutical composition according to this invention may be administered at a dosage capable of exhibiting a desired pharmacological activity without being accompanying with any appreciable side effect. Particular dosage is to be chosen by medical expert in each particular case, but the dosage of the active ingredient, the MI43-37F11 substance will, in general, be a level in the range of 10 mg–10 g, preferably 20 mg - 5 g, per day on adult patient for therapeutic treatments of carcinomas and malignant tumors. In these cases, the pharmaceutical composition of this invention may conveniently be administered as a unit preparation containing 1 m–5 g, preferably 3 mg–1 g of the active ingredient, MI43-37F11 substance.

Thus, according to a fourth aspect of this invention, there is provided a method of inhibitingly treating carcinomas or malignant tumor of mammalian animals, including man, which comprises administering the MI43-37F11 substance having formula (I) above, usually in the form of a pharmaceutical composition, in a therapeutically effective amount to a mammalian animal having a carcinoma or tumor.

As already mentioned briefly, the dosage of the MI43-37F11 substance may suitably be determined by medical experts typically having regard to the age, body weight, symptom of patients and therapeutic purpose as intended. The effective dosage as indicated above can be administered continuously or intermittently as long as the total dosage does not exceed such a specific level as decided in view of results of animal tests and various circumstances.

Furthermore, still another aspect of this invention include pharmaceutical use of the antibiotic, MI43-37F11 substance of the formula (I) as defined hereinbefore, as an anticancer or cancerocidal agent or as antitumor agent or in the manufacture thereof. This invention also include pharmaceutical use of the MI43-37F11 substance as an agent for enhancement of the production of interleukin-1 in vivo in a mammalian, including man, or in the manufacture of said agent. These agents may be in the form of a pharmaceutical composition comprising the MI43-37F11 substance as active ingredient, in association with a pharmaceutically acceptable carrier for the active ingredient.

Besides, as described hereinbefore, the MI43-37-F11 substance of this invention is effective to enable the peritoneal macrophages to make their increased production of 02- and also effective to enhance the phagocytic action of the macrophages as well as the in vivo production of interleukin-1, so that the MI43-37F11 substance of this invention is virtually able to enhance the activities of macrophages in vivo in a mammalian. Accordingly, a further aspect of this invention includes a use of the MI43-37F11 substance as an agent for activation of macrophage in vivo in a mammalian.

This invention is now illustrated with reference to the following Examples, to which this invention is not limited in any way.

EXAMPLE 1

A loopful amount of *Streptoverticillium eurocidicum* MI43-37F11 strain (identified as FERM BP-2783) was taken from its agar slant culture and then inoculated into 3 Elemmyer flasks which had each contained 110 ml of a sterilized culture medium comprising 2.0% galactose, 2.0% dextrin, 1.0% soy-pepton ("Bacto Soyton", a product of Difco Co., Ltd.), 0.5% corn steep liquor (a product of Nihon Shokuhin Kako Co., Ltd.), 0.2% ammonium sulfate, 0.2% calcium carbonate and 0.003% antifoaming agent, silicon oil "Silicon KM70" (a trade name of a product of Shinetsu Chemicals Co., Ltd.), as adjusted to pH 7.0. The inoculated culture media were then incubated at 30° C for 2 days under agitation, so that a seed culture was prepared.

2.5 ml -portions of the seed culture so obtained were each inoculated into 80 Sakaguchi flasks which had each contained 125 ml of a culture medium comprising 2.0% glycerine, 1.5% "Esusan Meat" (a trade name of a soybean flour product of Ajinomoto Co., Ltd.), 0.1% potassium hydrogen phosphate, 0.0005% cobalt chloride 6-hydrate and 0.003% antifoaming silicone, as adjusted to pH 6.2 with dipotassium phosphate. The cultivation of the MI43-37F11 strain was then conducted at 28° C. for 4 days. The resulting culture broth was filtered to remove the mycelia, and the recovered broth filtrate (adjusted to pH 5) was extracted with an equal volume of ethyl acetate. The resulting extract in ethyl acetate was concentrated under a reduced pressure to yield a brownish oily substance (2.0 g) containing the MI43-37F11 substance. 10 This crude product of the MI43-37F11 substance was mixed with 10 g of silica gel, followed by drying under reduced pressure. The resulting dried mixture was placed on the top of a column of 60 m( of silica gel, followed by carrying out a silica gel column chromatography. The silica gel column was previously packed with the silica gel with aid of n-hexane. The silica gel column having said mixture on the top thereof was first washed with a mixture (300 m() of n-hexane and ethyl acetate (8:2, V/V) and then eluted with a mixed solvent of n-hexane and ethyl acetate (1:1, V/V). The resulting eluate was concentrated under a reduced pressure to afford a brown colored oily substance (0.2 g) containing the MI43-37F11 substance.

This oily substance was mixed with 2 g of silica gel, followed by drying under reduced pressure. The resulting dried mixture was placed on the top of a column of 20 ml of a silica gel which had been packed into the column with aid of n-hexane. After this, for the column chromatography, the silica gel column having said mixture at the top thereof was first washed with 100 ml of a mixture of n-hexane-ethyl acetate(7:3, V/V) and then eluted with 100 m( of a mixture of n-hexane-ethyl acetate (6:4, V/V). The elute from the silica gel column was collected in 5 m(-fractions. The active fractions containing the MI43-37F11 substance were combined and concentrated under a reduced pressure to give 115 mg of a yellow colored oily substance.

This yellow oil product was dissolved in a small volume of acetonitrile and the solution was subjected to a high performance liquid chromatography on a reverse phase column (20 mm in diameter×300 mm in height) of octadodecyl silanide-coated silica gel (commercially available under a tradename "Senshu Pack" ODS 330IN, a product of Senshu Kagaku Co., Japan) in such a way that the elution was effected at a flow rate of 4 m(/minute with a linear concentration gradient from 20% acetonitrile to 50% acetonitrile in water. The eluate was collected in 4 m(-fractions. Among these collected fractions, the active fractions containing the MI43-37F11 substance were combined and concentrated in vacuo to afford 50 mg of a yellow colored powder comprising the MI43-37F11 substance.

This yellow powdery substance was again subjected to a high performance liquid chromatography on a silica gel column (20 mm in diameter×250 mm in height) of "YMC-Pack, A-043SIL" (a product commercially available from Yamamura Kagaku Kenkyujo Co., Japan) with a mixed solvent of n-hexane-chloroform (1:9, V/V) as eluent in such a way that the elution was effected at a flow rate of 4 m(/minute and the eluate was collected in 4 m(-fractions. The active fractions containing the MI43-37F11 substance were combined and concentrated in vacuo to afford 20 mg of a pale yellow colored powdery substance comprising the MI43-37F11 substance. This powdery substance was dissolved in a small volume of a mixture of chloroform-methanol (100: 1, V/V), and to the resulting solution was slowly added n-hexane so that a crystalline substance was deposited. This crystalline product was collected by filtration and dried to obtain 10 mg of a crystalline product of the MI43-37F11 substance which exhibited a melting point of 148.5-149.5° C.

This crystalline product showed a single spot on a silica gel thin layer chromatography on a silica gel plate (commercially available under a tradename "Art, 5715", a product of Merck Co., U.S.A.) as developed with chloroform-methanol (15:1, V/V), revealing that the MI43-37F11 substance in a pure form was obtained.

We claim:

1. An antibiotic, MI43-37F11 substance which is a compound having the formula

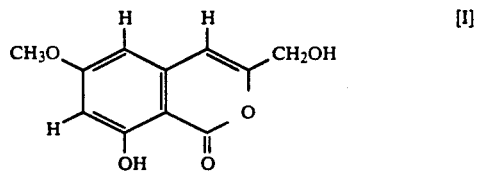

2. A pharmaceutical composition for inhibiting a carcinoma sensitive to the MI4337F11 substance comprising the MI43-37F11 substance having the formula as defined in claim 1, as active ingredient, in an amount effective to inhibit said carcinoma in association with a pharmaceutically acceptable carrier for the active ingredient.

* * * * *